United States Patent
Neuba et al.

(10) Patent No.: US 10,045,924 B2
(45) Date of Patent: Aug. 14, 2018

(54) MULTI-COMPONENT PACKAGING UNIT FOR OXIDATIVELY DYEING KERATIN FIBERS, HAVING REDUCED AMMONIA ODOR

(71) Applicant: Henkel AG & Co. KGaA, Duesseldorf (DE)

(72) Inventors: Constanze Neuba, Grevenbroich (DE); Burkhard Mueller, Duesseldorf (DE)

(73) Assignee: Henkel AG & Co. KGaA (DE)

( * ) Notice: Subject to any disclaimer, the term of this patent is extended or adjusted under 35 U.S.C. 154(b) by 0 days.

(21) Appl. No.: 15/016,367

(22) Filed: Feb. 5, 2016

(65) Prior Publication Data

US 2016/0151266 A1    Jun. 2, 2016

Related U.S. Application Data

(63) Continuation of application No. PCT/DE2014/200343, filed on Jul. 23, 2014.

(30) Foreign Application Priority Data

Aug. 7, 2013 (DE) .................. 10 2013 215 583

(51) Int. Cl.

| | | |
|---|---|---|
| A61Q 5/10 | (2006.01) | |
| A61K 8/49 | (2006.01) | |
| A61K 8/31 | (2006.01) | |
| A61K 8/34 | (2006.01) | |
| A61K 8/86 | (2006.01) | |
| A61K 8/19 | (2006.01) | |
| A61K 8/22 | (2006.01) | |
| A61K 8/41 | (2006.01) | |
| B65D 81/32 | (2006.01) | |

(52) U.S. Cl.
CPC .............. *A61K 8/4926* (2013.01); *A61K 8/19* (2013.01); *A61K 8/22* (2013.01); *A61K 8/31* (2013.01); *A61K 8/342* (2013.01); *A61K 8/411* (2013.01); *A61K 8/415* (2013.01); *A61K 8/86* (2013.01); *A61Q 5/10* (2013.01); *B65D 81/32* (2013.01); *A61K 2800/4324* (2013.01); *A61K 2800/882* (2013.01)

(58) Field of Classification Search
CPC . A61Q 5/10; A61K 8/342; A61K 8/86; A61K 8/411; A61K 8/22; A61K 8/19; A61K 8/4926; A61K 8/415; A61K 8/31; A61K 2800/4324; A61K 2800/882; B65D 81/32
See application file for complete search history.

(56) References Cited

U.S. PATENT DOCUMENTS

2008/0010754 A1*  1/2008  Bureiko ............... A61K 8/042
                                              8/406

FOREIGN PATENT DOCUMENTS

| JP | 2003-40750 A | 2/2003 | |
|---|---|---|---|
| JP | 2007-191459 A | 8/2007 | |
| JP | 2008-19220 A | 1/2008 | |
| JP | 2008-156252 | * 7/2008 | ............... A61Q 5/10 |
| JP | 2008-290949 A | 12/2008 | |
| JP | 2013-112641 A | 6/2013 | |
| WO | 2005/110499 A1 | 11/2005 | |
| WO | 2006/060565 A2 | 6/2006 | |
| WO | 2006/060570 A2 | 6/2006 | |

OTHER PUBLICATIONS

English abstract of the JP Patent No. 2008-156252 (Jul. 2008).*
English translation (Nov. 1, 2017) of the claims of the JP Patent No. JP 2008156252.*
PCT International Search Report (PCT/DE2014/200343) dated Sep. 1, 2015.
Database CA [Online], "Two-component Hair Bleaching or Dyeing Compositions Containing Higher Alcohols, Oils, and Cationic Surfactants", Chemical Abstracts Service, XP002734206, Database Accession No. 149:581968, 2007.

* cited by examiner

*Primary Examiner* — Eisa B Elhilo
(74) *Attorney, Agent, or Firm* — James J. Cummings

(57) ABSTRACT

A multi-component packaging unit (kit of parts) for oxidatively coloring keratin fibers, including two preparations (A) and (B) packaged separate from each other. Preparation (A) includes, in a cosmetic carrier, (a1) at least one oxidation dye precursor and (a2) ammonia, and preparation (B) includes, in a cosmetic carrier, (b1) hydrogen peroxide, (b2) at least one fatty alcohol from the group comprising arachidyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), heneicosyl alcohol (heneicosan-1-ol), behenyl alcohol (docosan-1-ol), erucyl alcohol ((13Z)-docos-13-en-1-ol), and/or brassidyl alcohol ((13E)-docosen-1-ol), and (b3) at least one hydrocarbon having 8 to 80 C atoms.

14 Claims, No Drawings

MULTI-COMPONENT PACKAGING UNIT FOR OXIDATIVELY DYEING KERATIN FIBERS, HAVING REDUCED AMMONIA ODOR

FIELD OF THE INVENTION

The present invention generally relates to cosmetics, and more particularly relates to multi-component packaging units (kit-of-parts) for the oxidative coloring of keratinic fibers, which comprise at least two preparations (A) and (B) produced separately from one another. The use of the application mixture prepared from (A) and (B) enables the oxidative coloring of keratin fibers and has a reduced ammonia odor. A further subject matter of the present invention is a method for the oxidative coloring of keratin fibers and the use of the kits to reduce the ammonia odor.

BACKGROUND OF THE INVENTION

The skilled artisan is familiar with a variety of coloring systems, depending on the requirement for the coloring, to provide color-changing cosmetic agents, particularly for keratinic fibers, such as, for example, hair. So-called oxidation coloring agents are used for permanent, intensive colors with suitable fastness properties. Such coloring agents typically include oxidation dye precursors, so-called developer components and coupler components, which together form the actual dyes under the influence of oxidizing agents, such as, for example, hydrogen peroxide. Oxidation coloring agents are characterized by excellent, long-lasting color results. The oxidizing agent (i.e., hydrogen peroxide), present in the oxidation coloring agent, in this case initiates not only the formation of the dyes, but it also breaks down oxidatively the hair's own color pigments (melanins), so that in the case of oxidative coloring, a lightening coloring is also possible simultaneously. In order to produce satisfactory coloring and lightening, oxidative coloring agents usually require an alkaline pH during use; optimal results are achieved in particular at pH values between 8.5 and 10.5.

Ammonia is the alkalizing agent of choice today for adjusting these pH values. Not only can the pH range necessary for dye formation be adjusted with ammonia, but ammonia also causes the swelling of hair to a greater degree than all other known alkalizing agents. At the same time, ammonia acts as a penetration agent or penetration aid, also to a greater extent than all other commercial alkalizing agents.

For these reasons, more intensive colors and significantly better gray coverage are obtained during use of ammonia in oxidative coloring agents in comparison with other alkalizing agents (such as, for example, potassium or sodium hydroxide, alkanolamines, or carbonates such as sodium carbonate or potassium carbonate).

Due to the greater color intensities from the outset, the fastness properties of the hair colors obtained with the aid of ammonia are also better. In particular, colored hair has the best washing fastness if ammonia was selected as the alkalizing agent.

The performance advantages associated with the use of ammonia are so diverse that ammonia is used in a great number of commercial oxidative coloring agents despite its unpleasant, pungent odor.

Extensive efforts to reduce the ammonia odor are already known from the literature. In this regard, there are three basic options for minimizing the odor: The literature gives as the first option the variation of the alkalizing agent and thereby the partial or total replacement of ammonia by odorless alternatives.

Thus, for example, there are a great number of formulations in which a mixture of ammonia and monoethanolamine or monoethanolamine alone is used as the alkalizing agent. A reduction in the ammonia content, however, generally results in a poorer penetration of the dyes into the hair, which as previously described is reflected particularly in poorer gray coverage and a poorer washing fastness. If the focus is on the development of especially lasting nuances, the use of monoethanolamine is not an option for this reason.

WO 2006060570 and WO 2006060565 propose the use of carbonates or carbonate sources as alkalizing agents for providing oxidative coloring agents with less of a pungent odor. It is also known from the literature, however, that carbonates in combination with oxidizing agents can damage hair to a greater extent. The additional hair damage caused by carbonates may be less problematic during use of the coloring agent on untreated or undamaged hair, but can add up to serious cumulative damage in persons who dye or bleach their hair regularly. If greater lightening and/or regular coloring are desired, the use of carbonates therefore is also not a feasible alternative.

A second basic option for reducing the ammonia odor is the addition of special perfume substances, which are intended to cover the ammonia odor. This approach is used, for example, in WO 2005/110499. Perfume substances can be unstable under alkaline storage conditions, however, so that there is the risk that the aromatic substances are broken down or changed structurally during storage, which is also reflected in an unpredictable change in the odor. Because corresponding changes are often perceptible only after several months or even years, the use of new or unknown perfumes is regarded as problematic.

A third basic option for reducing the ammonia odor is an optimization of the formulation. In this case, the carrier ingredients of the formulation are to be selected so that they assure optimal retention of the ammonia in the formulation and minimize its odor in this way. It is also known, however, that the formulation, the fatty substances it includes, its emulsifiers, surfactants, and the viscosity as well have a major effect on the coloring performance. When the formulation is modified, deterioration of the coloring performance must therefore be prevented in every case.

For example, JP 2007191459 proposes using cationic surfactants, phosphate esters, and aliphatic alcohols to reduce the ammonia odor in hair coloring agents.

JP 2003040750 discloses that the ammonia odor in bleaching agents is especially low if at least 5% of a crystalline component is added to the agents.

In particular, the lasting odor minimization over the entire application period is only very difficult to achieve. The time period within which the user of hair dyes is in contact with the coloring agent extends from the preparation of the application mixture, its application to hair and the treatment time, up to the washing out of the formulation. At typical treatment times of 30 to 45 minutes, the entire process can take up to 90 minutes, at most up to 2 hours. Covering the ammonia odor, which is effective for this entire time period, poses the ultimate challenge. There is a still greater need for optimization in this field specifically, and an optimal approach for a lasting reduction of the ammonia odor is not known in the state of the art so far.

It is therefore desirable to provide agents for the oxidative coloring and/or lightening of hair with a reduced ammonia odor. In this regard, the agents should not exhibit any decreases in their dyeing performance, particularly in their gray coverage and their washing fastness. Moreover, the use of the agents should not be associated with greater hair damage, and they should be easy to use and storage-stable.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

A multi-component packaging unit (kit-of-parts) for the oxidative coloring of keratinic fibers includes two preparations (A) and (B) packaged separate from one another. Preparation (A) includes in a cosmetic carrier; (a1) at least one oxidation dye precursor; and (a2) ammonia. Preparation (B) includes in a cosmetic carrier (b1) hydrogen peroxide; (b2) at least one fatty alcohol from the group comprising arachidyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), heneicosyl alcohol (heneicosan-1-ol), behenyl alcohol (docosan-1-ol), erucyl alcohol ((13Z)-docos-13-en-1-ol), and/or brassidyl alcohol ((13E)-docosen-1-ol); and (b3) at least one hydrocarbon having 8 to 80 C atoms.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The present invention is based on the finding that odor nuisance during the coloring process can be minimized if the agents are provided in the form of a multi-component packaging unit (kit-of-parts) that includes at least two preparations (A) and (B) packaged separate from one another, whereby component (B) thereof includes as special ingredients the combination of long-chain fatty alcohols and hydrocarbons.

A first subject matter of the present invention is a multi-component packaging unit (kit-of-parts) for the oxidative coloring of keratinic fibers, including two preparations (A) and (B) packaged separate from one another, whereby
(a) preparation (A) includes in a cosmetic carrier
(a1) at least one oxidation dye precursor and
(a2) ammonia, and
(b) preparation (B) includes in a cosmetic carrier
(b1) hydrogen peroxide,
(b2) at least one fatty alcohol from the group comprising arachidyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), heneicosyl alcohol (heneicosan-1-ol), behenyl alcohol (docosan-1-ol), erucyl alcohol ((13Z)-docos-13-en-1-ol), and/or brassidyl alcohol ((13E)-docosen-1-ol), and
(b3) at least one hydrocarbon having 8 to 80 C atoms.

Keratin-containing fibers are understood in principle to be all animal hair, e.g., wool, horsehair, angora hair, fur, feathers, and products or textiles manufactured therefrom. Preferably, however, the keratinic fibers are human hair.

Preparations (A) and (B) include the components, essential to the invention, in each case in a cosmetic carrier, preferably in a suitable aqueous, alcoholic, or aqueous-alcoholic carrier. For the purpose of oxidative coloring, such carriers can be, for example, creams, emulsions, gels, or surfactant-containing foaming solutions as well, such as, for example, shampoos, foam aerosols, foam formulations, or other preparations suitable for use on hair.

The oxidation coloring agent of the invention comprises at least two preparations (A) and (B) packaged separate from one another. The two preparations are mixed together shortly before use. The ready-to-use coloring agent applied to the keratin fibers is prepared in this way.

Preparations (A) and (B), packaged separate from one another, can be provided in separate containers, which are located together in an outer package (e.g., a cardboard box or a carton). It is also inventive, however, to provide preparations (A) and (B) in two separate containers, which are purchased separately from one another (for example, within a series of products) and are mixed together before use.

It is also possible and inventive, furthermore, that the ready-to-use coloring agent is prepared before use from three components packaged separate from one another. In this case, the three components (A), (B), and (C) are mixed together before use and the application mixture resulting after the mixing of the three preparations is applied to the keratin fibers. The three components (A), (B), and (C) as well can be provided to the consumer in three separate containers, which are located within a common outer package, or completely separated, however, (e.g., within a series of products).

It is preferred if the ready-to-use oxidation coloring agent is prepared by mixing only two preparations (A) and (B).

Preparation (A) present in the multi-component packaging unit (kit-of-parts) is a dye cream, which includes in a cosmetic carrier at least one oxidation dye precursors (a1) and the ammonia (a2) necessary for swelling, penetration, and alkalinization.

The oxidation dye precursors (a1) include oxidation dye precursors of the developer type and of the coupler type. Preferred oxidation dye precursors of the developer type are selected from at least one compound from the group comprising p-phenylenediamine, p-toluylenediamine, 2-(2-hydroxyethyl)-p-phenylenediamine, 2-(1,2-dihydroxyethyl)-p-phenylenediamine, N,N-bis(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis(2-hydroxyethyl)-N,N'-bis(4-aminophenyl)-1,3-diaminopropan-2-ol, bis(2-hydroxy-5-aminophenyl)methane, 1,3-bis(2,5-diaminophenoxy)propan-2-ol, N,N'-bis(4-aminophenyl)-1,4-diazacycloheptane, 1,10-bis(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl)phenol, 4,5-diamino-1-(2-hydroxyethyl)-1H-pyrazole, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo[1,2-a]pyrazol-1-one, and the physiologically acceptable salts thereof.

Especially preferred oxidation dye precursors of the developer type are selected from the group comprising p-toluylenediamine, 2-(2-hydroxyethyl)-p-phenylenediamine, 2-methoxymethyl-p-phenylenediamine, N-(4-amino-3-methylphenyl)-N-[3-(1H-imidazol-1-yl)propyl]amine, bis(2-hydroxy-5-aminophenyl)methane, p-aminophenol, 4-amino-3-methylphenol, 4,5-diamino-1-(2-hydroxyethyl)-1H-pyrazole, 2,4,5,6-tetraaminopyrimidine, 4-hydroxy-2,5, 6-triaminopyrimidine, 2-hydroxy-4,5,6-triaminopyrimidine, and the physiologically acceptable salts thereof.

Coupler components during the oxidative coloring alone cause no significant coloring, but always require the presence of developer components. Coupler components within the meaning of the invention permit at least one substitution of a chemical group of the coupler by the oxidized form of the developer component. In this regard, a covalent bond forms between the coupler and developer component.

Especially suitable oxidation dye precursors of the coupler type are selected from the group comprising 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}-amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline, or mixtures of said compounds or the physiologically acceptable salts thereof.

Preparation (A) can include the oxidation dye precursors (developer and coupler) in a total amount of 0.01 to 6.5% by weight, preferably of 0.05 to 5.5% by weight, more preferably of 0.1 to 4.5% by weight, and particularly preferably of 0.3 to 4.0% by weight, based on the total weight of preparation (A).

In addition to the oxidation dye precursors, preparation (A) can also include one or more direct dyes. Direct dyes can be divided into anionic, cationic, and nonionic direct dyes. The direct dyes are preferably selected from nitrophenylenediamines, nitroaminophenols, azo dyes, anthraquinones, triarylmethane dyes, or indophenols, and the physiologically acceptable salts thereof.

Especially preferably, this concerns one or more nonionic direct dyes from the group comprising HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9,1,4-diamino-2-nitrobenzene, 2-amino-4-nitrophenol, 1,4-bis(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 4-[(3-hydroxypropyl)amino]-3-nitrophenol, 4-nitro-o-phenylenediamine, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid, and 2-chloro-6-ethylamino-4-nitrophenol.

One or more compounds may also be present as direct dyes, said compounds which are known under the international names or trade names: Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, bromophenol blue, and tetrabromophenol blue.

Suitable cationic direct dyes are cationic triphenylmethane dyes, such as, for example, Basic Blue 7, Basic Blue 26, Basic Violet 2, and Basic Violet 14, aromatic systems, substituted with a quaternary nitrogen group, such as, for example, Basic Yellow 57, Basic Red 76, Basic Blue 99, Basic Brown 16, and Basic Brown 17, cationic anthraquinone dyes, such as HC Blue 16 (Bluequat B), and direct dyes, including a heterocycle that has at least one quaternary nitrogen atom, particularly Basic Yellow 87, Basic Orange 31, and Basic Red 51. The cationic direct dyes, which are marketed under the trademark Arianor, are also suitable cationic direct dyes according to the invention.

In addition, direct dyes present in preparation (A) can be used in a total amount of 0.001 to 4.0% by weight, preferably of 0.01 to 3.0% by weight, more preferably of 0.05 to 2.0% by weight, and very especially preferably of 0.1 to 1.5% by weight, based on the total weight of preparation (A).

Preparation (A) includes as the second essential component ammonia (a2).

Ammonia ($NH_3$) is customarily employed in the form of its aqueous solution, in which it is present in the form of ammonium hydroxide ($NH_4OH$). Aqueous ammonia solutions include ammonia ($NH_3$) often in concentrations between 10% by weight and 32% by weight. Preferred in this case is the use of an aqueous ammonia solution, which includes 25% by weight of ammonia ($NH_3$).

Because ammonia is used primarily as an alkalizing agent, its use amounts depend on the pH that the ready-to-use oxidation coloring agent is to have. The skilled artisan knows that the pH of preparation (A) also increases with an increasing ammonia amount. When preparations (A) and (B) are mixed, the ammonia content thus also determines the pH of the application mixture.

Coloring processes on keratin fibers typically take place in an alkaline environment. To treat keratin fibers and the skin as well as gently as possible, setting a too high pH is not desirable, however. It is preferred, therefore, that the amount of ammonia used is selected so that the pH of the ready-to-use agent is between 7 and 11, particularly between 8 and 10.5. pH values within the meaning of the present invention are pH values measured at a temperature of 22° C.

Ammonia amounts of 0.1 to 6.0% by weight, preferably of 0.3 to 4.5% by weight, more preferably of 0.4 to 3.0% by weight, and particularly preferably of 0.5 to 2.5% by weight of ammonia, based on the amount of ammonia (NH3) in the total amount of preparation (A), can be used to adjust these pH values, depending on other acids, buffers, or other alkalizing agents present in the application mixture.

Preparation (B) is the component that includes the oxidizing agents.

Preparations (B) of the invention are characterized in that they include in a cosmetic carrier hydrogen peroxide (b1), special long-chain fatty alcohols (b2), and hydrocarbons (b3).

It emerged during the work leading to this invention that the combination of special long-chain fatty alcohols (b2) and hydrocarbons (b3) is excellently suitable for suppressing the odor perception of ammonia during use.

It was found surprisingly hereby that the odor suppression is the most effective when the combination of fatty alcohols (b2) and hydrocarbons (b3) is present not in the dye cream (i.e., preparation (A)), but in preparation (B) including the oxidizing agent.

The fact that the ammonia odor can be suppressed more greatly if ammonia (a2) and fatty alcohols (b2)/hydrocarbons (b3) are stored separated and are combined only shortly before use was not foreseeable for the skilled artisan. A possible explanation for this unexpected effect could be a special, temporary emulsion form, which forms shortly after the mixing process between ammonia and components (b2)/(b3).

Preparation (B) includes hydrogen peroxide (b1) as the first essential ingredient. In a preferred embodiment, hydrogen peroxide itself is used as an aqueous solution. The concentration of a hydrogen peroxide solution in the agent of the invention is determined, on the one hand, by legal requirements and, on the other, by the desired effect; preferably, 6 to 12% by weight solutions in water are used.

Preparations (B) preferred according to the invention are characterized in that they include 0.5 to 20% by weight, preferably 1 to 12.5% by weight, particularly preferably 2.5 to 10% by weight, and particularly 3 to 9% by weight of hydrogen peroxide, based in each case on the total weight of preparation (B).

Preparation (B) includes as the second ingredient, essential to the invention, at least one fatty alcohol (b2) from the group comprising arachidyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), heneicosyl alcohol (heneicosan-1-ol), behenyl alcohol (docosan-1-ol), erucyl alcohol ((13Z)-docos-13-en-1-ol), and/or brassidyl alcohol ((13E)-docosen-1-ol).

These long-chain fatty alcohols (b2) have a chain length of at least 20 C atoms. Within this group, special long-chain fatty alcohols have proven to be very especially suitable in regard to odor optimization of the application mixtures.

In an especially preferred embodiment, preparation (B) is characterized in that it includes arachidyl alcohol (eicosan-1-ol).

In another especially preferred embodiment, preparation (B) is characterized in that it includes behenyl alcohol (docosan-1-ol).

In another especially preferred embodiment, preparation (B) is characterized in that it includes arachidyl alcohol (eicosan-1-ol) and/or behenyl alcohol (docosan-1-ol).

It emerged, furthermore, that it is of advantage, if the long-chain fatty alcohols (b2), particularly arachidyl alcohol (eicosan-1-ol) and/or behenyl alcohol (docosan-1-ol), are present in preparation (B) within specific amount ranges. It has proven especially preferable hereby, if the total amount of fatty alcohols (b2) is selected sufficiently high, so that an effective reduction of the ammonia odor can be achieved. On the other hand, too high use amounts of fatty alcohols (b2) have proven disadvantageous, because the coloring agent in the last case is thickened too greatly. Due to the too high viscosity, the diffusion of the active species (oxidizing agents) into the hair shaft is prevented, which results in the worsening of the coloring performance.

Based on these findings, it has proven especially advantageous, if preparation (B) includes one or more long-chain fatty alcohols (b2) from the group comprising arachidyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), heneicosyl alcohol (heneicosan-1-ol), behenyl alcohol (docosan-1-ol), erucyl alcohol ((13Z)-docos-13-en-1-ol), and brassidyl alcohol ((13E)-docosen-1-ol) in a total amount of 0.2 to 6.4% by weight, preferably of 0.3 to 4.4% by weight, more preferably of 0.4 to 2.4% by weight, and particularly preferably of 0.5 to 1.4% by weight, based on the total weight of preparation (B).

In a very especially preferred embodiment, a multi-component packaging unit (kit-of-parts) of the invention is therefore characterized in that preparation (B) includes as the fatty alcohol(s) (b2) arachidyl alcohol (eicosan-1-ol) and/or behenyl alcohol (docosan-1-ol) in a total amount of 0.2 to 6.4% by weight, preferably of 0.3 to 4.4% by weight, more preferably of 0.4 to 2.4% by weight, and particularly preferably of 0.5 to 1.4% by weight, based on the total weight of preparation (B).

Apart from the special long-chain fatty alcohols (b2) with a chain length of at least 20 C atoms, preparation (A) and/or (B) can include in addition also still other, shorter-chain fatty alcohols with a chain length of 12 to 18 C atoms. Suitable shorter-chain fatty alcohols with a saturated $C_{12}$-$C_{18}$ alkyl chain are, for example, dodecan-1-ol (dodecyl alcohol, lauryl alcohol), tetradecan-1-ol (tetradecyl alcohol, myristyl alcohol), hexadecan-1-ol (hexadecyl alcohol, cetyl alcohol, palmityl alcohol), and octadecan-1-ol (octadecyl alcohol, stearyl alcohol). A suitable shorter-chain fatty alcohol with an unsaturated $C_{12}$-$C_{18}$ alkyl chain is, for example, (9Z)-octadec-9-en-1-ol (oleyl alcohol).

Preparation (B) can include the shorter-chain fatty alcohols with a chain length of 12 to 18 C atoms in a total amount of 0.1 to 6.0% by weight, preferably of 0.3 to 5.0% by weight, and particularly preferably of 0.5 to 4.0% by weight, based on the total weight of preparation (B).

Preparation (A) as well can include shorter-chain fatty alcohols with a chain length of 12 to 18 C atoms. Preparation (A) can include the shorter-chain fatty alcohols with a chain length of 12 to 18 C atoms in a total amount of 0.1 to 12.0% by weight, preferably of 0.3 to 10.0% by weight, and particularly preferably of 0.5 to 8.0% by weight, based on the total weight of preparation (A).

Preparation (B) includes as the third component, essential to the invention, at least one hydrocarbon (b3) having 8 to 80 C atoms. Hydrocarbons having 8 to 80 C atoms within the meaning of the invention are understood to mean compounds that consist exclusively of carbon and hydrogen. Preferred in this regard are particularly aliphatic hydrocarbons such as, for example, mineral oils, liquid paraffin oils (e.g., liquid paraffin or light liquid paraffin), isoparaffin oils, semisolid paraffin oils, paraffin waxes, hard paraffin (solid paraffin), Vaseline, and polydecene.

It turned out that the C-chain distribution of the paraffin oils also has an effect on the effectiveness of the odor reduction. Liquid paraffin oils (liquid paraffin and light liquid paraffin) have proven to be especially suitable in this regard. The hydrocarbon (b3) is very especially preferably liquid paraffin, also called white oil. Liquid paraffin is a mixture of purified, saturated, aliphatic hydrocarbons, which consists for the most part of hydrocarbon chains with a C-chain distribution of 25 to 35 C atoms.

Especially preferred, therefore, is a multi-component packaging unit (kit-of-parts) for the oxidative coloring of keratinic fibers, comprising two preparations (A) and (B) packaged separate from one another, whereby
(a) preparation (A) includes in a cosmetic carrier
(a1) at least one oxidation dye precursor and
(a2) ammonia, and (b) preparation (B) includes in a cosmetic carrier
(b1) hydrogen peroxide,
(b2) at least one fatty alcohol from the group comprising arachidyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), heneicosyl alcohol (heneicosan-1-ol), behenyl alcohol (docosan-1-ol), erucyl alcohol ((13Z)-docos-13-en-1-ol), and/or brassidyl alcohol ((13E)-docosen-1-ol), and
(b3) at least one hydrocarbon having 25 to 35 C atoms.

Likewise preferred is also a multi-component packaging unit (kit-of-parts) for the oxidative coloring of keratinic fibers, comprising two preparations (A) and (B) packaged separate from one another, whereby
(a) preparation (A) includes in a cosmetic carrier
(a1) at least one oxidation dye precursor and
(a2) ammonia, and
(b) preparation (B) includes in a cosmetic carrier
(b1) hydrogen peroxide,
(b2) at least one fatty alcohol from the group comprising arachidyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), heneicosyl alcohol (heneicosan-1-ol), behenyl alcohol (docosan-1-ol), erucyl alcohol ((13Z)-docos-13-en-1-ol), and/or brassidyl alcohol ((13E)-docosen-1-ol), and
(b3) paraffin oil.

Preferred furthermore is a multi-component packaging unit (kit-of-parts) for the oxidative coloring of keratinic fibers, comprising two preparations (A) and (B) packaged separate from one another, whereby
(a) preparation (A) includes in a cosmetic carrier
(a1) at least one oxidation dye precursor and
(a2) ammonia, and
(b) preparation (B) includes in a cosmetic carrier
(b1) hydrogen peroxide,
(b2) at least one fatty alcohol from the group comprising arachidyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), heneicosyl alcohol (heneicosan-1-ol), behenyl alcohol (docosan-1-ol), erucyl alcohol ((13Z)-docos-13-en-1-ol), and/or brassidyl alcohol ((13E)-docosen-1-ol), and
(b3) paraffin wax.

Preferably, hydrocarbons (b3) with 8 to 80 C atoms are used in specific amount ranges. In another preferred embodiment, preparation (B) includes the hydrocarbon(s) having 8 to 80 C atoms (b3) in a total amount of 0.1 to 4.5% by weight, preferably of 0.2 to 3.2% by weight, more preferably of 0.3 to 1.8% by weight, and particularly preferably of 0.4 to 0.9% by weight, based on the total weight of preparation (B).

A very especially preferred multi-component packaging unit (kit-of-parts) is characterized in that preparation (B) includes as the hydrocarbon(s) (b3) one or more paraffin oils and/or one or more paraffin waxes in a total amount of 0.1 to 4.5% by weight, preferably of 0.2 to 3.2% by weight, more preferably of 0.3 to 1.8% by weight, and particularly preferably of 0.4 to 0.9% by weight, based on the total weight of preparation (B).

Tests conducted within the scope of this invention have shown that there is an interaction between the long-chain fatty alcohols (b2) and the hydrocarbons (b3).

The use of the long-chain fatty alcohols (b2) without hydrocarbons (particularly without liquid paraffin) leads to a less satisfactory suppression of the ammonia odor. If both components (b2) and (b3) are used together, the perception of odor was considerably reduced. In this regard, the ammonia odor could be reduced particularly if components (b2) and (b3) were used in specific, mutually matched mass ratios. A weight ratio (b2)/(b3) of 15:1 to 1:1, preferably of 10:1 to 1:1, more preferably of 7:1 to 1:1, and particularly preferably of 3:1 to 2:1 has produced the best results in this regard.

Thus, the object of the invention was achieved particularly well when the long-chain fatty alcohols (b2) were used in an excess in comparison with the hydrocarbons (b3).

For this reason, another very especially preferred multi-component packaging unit (kit-of-parts) is characterized in that preparation (B) includes the fatty alcohol(s) (b2) and the aliphatic hydrocarbon(s) (b3) in a weight ratio (b2)/(b3) of 15:1 to 1:1, preferably of 10:1 to 1:1, more preferably of 7:1 to 1:1, and particularly preferably of 3:1 to 2:1.

The weight ratios (b2)/(b3) cited in this regard refer hereby in each case to the total amount of all long-chain fatty alcohols (b2), present in preparation (B), which are placed in a weight relation to the total amount of all hydrocarbons (b3) present in preparation (B).

It turned out, furthermore, that preparation (B) can be optimized still further by the use of additional special ingredients in regard to the retention of the ammonia odor. Highly ethoxylated fatty alcohols primarily have proven very effective in this regard. If preparation (B) includes in addition at least one ethoxylated fatty alcohol (b4) with a degree of ethoxylation of 80 to 120, thus the odor minimization continues to be significantly perceptible for an especially long time period.

In another especially preferred embodiment, a multi-component packaging unit of the invention is therefore characterized in that preparation (B) includes in addition (b4) at least one ethoxylated fatty alcohol of the formula (I),

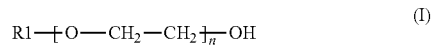

$$R1-\!\!+\!\!O-CH_2-CH_2\!\!+\!\!_n\!\!-OH \qquad (I)$$

where
R1 stands for an unbranched or branched, saturated or unsaturated $C_{12}$-$C_{28}$ alkyl group, preferably for a saturated, unbranched $C_{16}$ or $C_{18}$ alkyl group, and
n stands for an integer from 80 to 120, preferably for an integer from 85 to 115, more preferably for an integer from 90 to 110, and particularly preferably for an integer from 95 to 105.

Advantageous in particular is the addition of ethoxylated fatty alcohols of the formula (I), in which n stands for a number from 95 to 110.

Ethoxylated fatty alcohols of the formula (I), in which R1 stands for a saturated, linear C16 alkyl group or for a saturated, linear C18 alkyl group, are also very especially preferred.

Stearyl alcohol, ethoxylated with 100 ethylene oxide units (INCI name: Steareth-100, CAS No. 9005-00-9), which is sold, for example, under the trade name Brij S 100 or Brij 700 P by the company Croda, can be cited as an example for these especially preferred representatives.

Especially preferred, furthermore, therefore, is a multi-component packaging unit (kit-of-parts) for the oxidative coloring of keratinic fibers, comprising two preparations (A) and (B) packaged separate from one another, whereby
(a) preparation (A) includes in a cosmetic carrier
(a1) at least one oxidation dye precursor and
(a2) ammonia, and (b) preparation (B) includes in a cosmetic carrier
(b1) hydrogen peroxide,
(b2) at least one fatty alcohol from the group comprising arachidyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), heneicosyl alcohol (heneicosan-1-ol), behenyl alcohol (docosan-1-ol), erucyl alcohol ((13Z)-docos-13-en-1-ol), and/or brassidyl alcohol ((13E)-docosen-1-ol),
(b3) paraffin oil, and
(b4) at least one ethoxylated fatty alcohol of the formula (I),

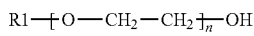

where
R1 stands for a saturated, unbranched $C_{16}$ or $C_{18}$ alkyl group, and
n stands for an integer from 95 to 105.

Especially preferred hereby is a multi-component packaging unit (kit-of-parts) for the oxidative coloring of keratinic fibers, comprising two preparations (A) and (B) packaged separate from one another, whereby
(a) preparation (A) includes in a cosmetic carrier
(a1) at least one oxidation dye precursor and
(a2) ammonia, and
(b) preparation (B) includes in a cosmetic carrier
(b1) hydrogen peroxide,
(b2) at least one fatty alcohol from the group comprising arachidyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), heneicosyl alcohol (heneicosan-1-ol), behenyl alcohol (docosan-1-ol), erucyl alcohol ((13Z)-docos-13-en-1-ol), and/or brassidyl alcohol ((13E)-docosen-1-ol)
(b3) paraffin oil, and
(b4) steareth-100.

The ethoxylated fatty alcohols (b4) of the formula (I) are used advantageously in specific amount ranges in preparation (B).

Preferred multi-component packaging units are therefore notable in that preparation (B) includes one or more ethoxylated fatty alcohols (b4) of the formula (I) in a total amount of 0.1 to 5.5% by weight, preferably of 0.2 to 3.8% by weight, more preferably of 0.3 to 2.6% by weight, and particularly preferably of 0.4 to 1.1% by weight, based on the total weight of preparation (B).

It has also proven advantageous, if preparation (A) of the multi-component kit itself includes no ethoxylated fatty alcohols of the formula (I), i.e., if preparation (A) is free of ethoxylated fatty alcohols of the formula (I).

In another preferred embodiment, the multi-component packaging unit (kit-of-parts) is characterized in that preparation (A) is free of ethoxylated fatty alcohol of the formula (I).

Understood under the definition "free of ethoxylated fatty alcohols of the formula (I)" in this context are preparations (A) that include less than 0.5% by weight, more preferably less than 0.4% by weight, even more preferably less than 0.1% by weight, and particularly preferably less than 0.05% by weight of ethoxylated fatty alcohols of the formula (I). The calculation basis for the indicated amounts hereby is the total weight of preparation (A).

Preferred accordingly is a multi-component packaging unit (kit-of-parts) for the oxidative coloring of keratinic fibers, comprising two preparations (A) and (B) packaged separate from one another, whereby
(a) preparation (A) includes in a cosmetic carrier
(a1) at least one oxidation dye precursor and
(a2) ammonia,
(a3) is free of ethoxylated fatty alcohols of the formula (I),

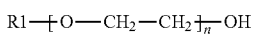

where
R1 stands for a saturated, unbranched $C_{16}$ or $C_{18}$ alkyl group, and
n stands for an integer from 80 to 120,
(b) preparation (B) includes in a cosmetic carrier
(b1) hydrogen peroxide,
(b2) at least one fatty alcohol from the group comprising arachidyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), heneicosyl alcohol (heneicosan-1-ol), behenyl alcohol (docosan-1-ol), erucyl alcohol ((13Z)-docos-13-en-1-ol), and/or brassidyl alcohol ((13E)-docosen-1-ol)
(b3) paraffin oil, and
(b4) at least one ethoxylated fatty alcohol of the formula (I),

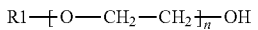

where
R1 stands for an unbranched or branched, saturated or unsaturated $C_{12}$-$C_{28}$ alkyl group, preferably for a saturated, unbranched $C_{16}$ or $C_{18}$ alkyl group, and
n stands for an integer from 80 to 120, preferably for an integer from 85 to 115, more preferably for an integer from 90 to 110, and particularly preferably for an integer from 95 to 105.

Preferred accordingly is a multi-component packaging unit (kit-of-parts) for the oxidative coloring of keratinic fibers, comprising two preparations (A) and (B) packaged separate from one another, whereby
(a) preparation (A) includes in a cosmetic carrier
(a1) at least one oxidation dye precursor and
(a2) ammonia, and
(a3) includes less than 0.1% by weight of ethoxylated fatty alcohols of the formula (I)

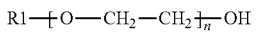

where
R1 stands for a saturated, unbranched $C_{16}$ or $C_{18}$ alkyl group, and
n stands for an integer from 80 to 120,
(b) preparation (B) includes in a cosmetic carrier
(b1) hydrogen peroxide,
(b2) at least one fatty alcohol from the group comprising arachidyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), heneicosyl alcohol (heneicosan-1-ol), behenyl alcohol (docosan-1-ol), erucyl alcohol ((13Z)-docos-13-en-1-ol), and/or brassidyl alcohol ((13E)-docosen-1-ol), (b3) paraffin oil, and
(b4) at least one ethoxylated fatty alcohol of the formula (I), $$R1\!-\!\!\left[O\!-\!CH_2\!-\!CH_2\right]_{\!n}\!\!-\!OH \qquad (I)$$

where
R1 stands for an unbranched or branched, saturated or unsaturated $C_{12}$-$C_{28}$ alkyl group, preferably for a saturated, unbranched $C_{16}$ or $C_{18}$ alkyl group, and
n stands for an integer from 80 to 120, preferably for an integer from 85 to 115, more preferably for an integer from 90 to 110, and particularly preferably for an integer from 95 to 105.

To achieve a maximum covering up of the odor, the long-chain fatty alcohols (b2) and the ethoxylated fatty alcohols (b4) of the formula (I) are also used in an optimized weight ratio relative to one another. It is of advantage in this regard if the fatty alcohol (b2) is used in a higher amount than the ethoxylated fatty alcohol (b4).

If, in contrast, the ethoxylated fatty alcohol (b4) is used in excess in comparison with the long-chain fatty alcohol (b2), then worsening of the odor covering up can again be observed.

For this reason, another especially preferred multi-component packaging unit is characterized in that composition (B) includes the fatty alcohol(s) (b2) and the ethoxylated fatty alcohol(s) (b4) of the formula (I) in a weight ratio (b2)/(b4) of 10:1 to 1:1, preferably of 5:1 to 1:1, more preferably of 4:1 to 1:1, and particularly preferably of 3:1 to 2:1.

The weight ratio (b2)/(b4) quantifies hereby the weight ratio of the total amount of all long-chain fatty alcohols (b2) present in formulation (B) to the total amount of all ethoxylated fatty alcohols (b4), present in formulation (B), of the formula (I).

It is also of particular advantage to achieve the object of the invention if the hydrocarbons (b3) and the ethoxylated fatty alcohols (b4) of the formula (I) are used in a specific weight ratio to one another.

Thereby, another especially preferred multi-component packaging unit (kit-of-parts) is characterized in that composition (B) includes the aliphatic hydrocarbon(s) (b3) and the ethoxylated fatty alcohol(s) (b4) in a weight ratio (b3)/(b4) of 5:1 to 1:5, preferably of 3:1 to 1:3, more preferably of 2:1 to 1:2, and particularly preferably of 2:1 to 1:1.

Taking account the aforementioned preferred and especially preferred embodiments, a multi-component packaging unit is particularly preferred that comprises two preparations (A) and (B) packaged separate from one another, whereby
(a) preparation (A) includes in a cosmetic carrier
(a1) at least one oxidation dye precursor and
(a2) ammonia, and
(b) preparation (B) includes in a cosmetic carrier
(b1) hydrogen peroxide,
(b2) 0.2 to 6.4% by weight of arachidyl alcohol (eicosan-1-ol) and/or behenyl alcohol (docosan-1-ol),
(b3) 0.1 to 4.5% by weight of paraffin oil,
whereby the weight data in each case refer to the total weight of preparation (B).

In another embodiment, a multi-component packaging unit is particularly preferred, which comprises two preparations (A) and (B) packaged separate from one another, whereby
(a) preparation (A) includes in a cosmetic carrier
(a1) at least one oxidation dye precursor and
(a2) ammonia, and
(b) preparation (B) includes in a cosmetic carrier
(b1) hydrogen peroxide,
(b2) 0.3 to 4.4% by weight of arachidyl alcohol (eicosan-1-ol) and/or behenyl alcohol (docosan-1-ol),
(b3) 0.2 to 3.2% by weight of paraffin oil,
whereby the weight data in each case refer to the total weight of preparation (B).

In another embodiment, a multi-component packaging unit is particularly preferred, which comprises two preparations (A) and (B) packaged separate from one another, whereby
(a) preparation (A) includes in a cosmetic carrier
(a1) at least one oxidation dye precursor and
(a2) ammonia, and
(b) preparation (B) includes in a cosmetic carrier
(b1) hydrogen peroxide,
(b2) 0.4 to 2.4% by weight of arachidyl alcohol (eicosan-1-ol) and/or behenyl alcohol (docosan-1-ol),
(b3) 0.3 to 1.8% by weight of paraffin oil,
whereby the weight data in each case refer to the total weight of preparation (B).

In another embodiment, a multi-component packaging unit is particularly preferred, which comprises two preparations (A) and (B) packaged separate from one another, whereby
(a) preparation (A) includes in a cosmetic carrier
(a1) at least one oxidation dye precursor and
(a2) ammonia, and
(b) preparation (B) includes in a cosmetic carrier
(b1) hydrogen peroxide,
(b2) 0.5 to 1.4% by weight of arachidyl alcohol (eicosan-1-ol) and/or behenyl alcohol (docosan-1-ol),
(b3) 0.4 to 0.9% by weight of paraffin oil,
whereby the weight data in each case refer to the total weight of preparation (B).

In another embodiment, a multi-component packaging unit is particularly preferred, which comprises two preparations (A) and (B) packaged separate from one another, whereby
(a) preparation (A) includes in a cosmetic carrier
(a1) at least one oxidation dye precursor and
(a2) ammonia, and
(b) preparation (B) includes in a cosmetic carrier
(b1) hydrogen peroxide,
(b2) at least one fatty alcohol from the group comprising arachidyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), heneicosyl alcohol (heneicosan-1-ol), behenyl alcohol (docosan-1-ol), erucyl alcohol ((13Z)-docos-13-en-1-ol), and/or brassidyl alcohol ((13E)-docosen-1-ol),
(b3) at least one hydrocarbon having 8 to 80 C atoms, and
(b4) at least one ethoxylated fatty alcohol of the formula (I), $$R1\!-\!\!\left[O\!-\!CH_2\!-\!CH_2\right]_{\!n}\!\!-\!OH \qquad (I)$$

where
R1 stands for an unbranched or branched, saturated or unsaturated $C_{12}$-$C_{28}$ alkyl group, preferably for a saturated, unbranched $C_{16}$ or $C_{18}$ alkyl group, and n stands for an integer from 80 to 120, preferably for an integer from 85 to 115, more preferably for an integer from 90 to 110, and particularly preferably for an integer from 95 to 105,
and preparation (B) includes the fatty alcohol(s) (b2) and the hydrocarbon(s) (b3) in a weight ratio (b2)/(b3) of 15:1 to 1:1, preferably of 10:1 to 1:1, more preferably of 7:1 to 1:1, and particularly preferably of 3:1 to 2:1.

In another embodiment, a multi-component packaging unit is particularly preferred, which comprises two preparations (A) and (B) packaged separate from one another, whereby
(a) preparation (A) includes in a cosmetic carrier
(a1) at least one oxidation dye precursor and
(a2) ammonia, and
(b) preparation (B) includes in a cosmetic carrier
(b1) hydrogen peroxide,
(b2) at least one fatty alcohol from the group comprising arachidyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), heneicosyl alcohol (heneicosan-1-ol), behenyl alcohol (docosan-1-ol), erucyl alcohol ((13Z)-docos-13-en-1-ol), and/or brassidyl alcohol ((13E)-docosen-1-ol),
(b3) at least one hydrocarbon having 8 to 80 C atoms, and
(b4) at least one ethoxylated fatty alcohol of the formula (I),

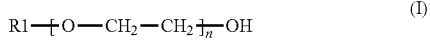

$$R1 \!\!-\!\![O\!-\!CH_2\!-\!CH_2]_{\overline{n}}\!-\!OH \quad (I)$$

where
R1 stands for an unbranched or branched, saturated or unsaturated $C_{12}$-$C_{28}$ alkyl group, preferably for a saturated, unbranched $C_{16}$ or $C_{18}$ alkyl group, and
n stands for an integer from 80 to 120, preferably for an integer from 85 to 115, more preferably for an integer from 90 to 110, and particularly preferably for an integer from 95 to 105,
and composition (B) includes the fatty alcohol(s) (b2) and the ethoxylated fatty alcohol(s)
(b4) of the formula (I) in a weight ratio (b2)/(b4) of 10:1 to 1:1, preferably of 5:1 to 1:1, more preferably of 4:1 to 1:1, and particularly preferably of 3:1 to 2:1.

In another embodiment, a multi-component packaging unit is particularly preferred, which comprises two preparations (A) and (B) packaged separate from one another, whereby
(a) preparation (A) includes in a cosmetic carrier
(a1) at least one oxidation dye precursor and
(a2) ammonia, and
(b) preparation (B) includes in a cosmetic carrier
(b1) hydrogen peroxide,
(b2) at least one fatty alcohol from the group comprising arachidyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), heneicosyl alcohol (heneicosan-1-ol), behenyl alcohol (docosan-1-ol), erucyl alcohol ((13Z)-docos-13-en-1-ol), and/or brassidyl alcohol ((13E)-docosen-1-ol),
(b3) at least one hydrocarbon having 8 to 80 C atoms, and
(b4) at least one ethoxylated fatty alcohol of the formula (I),

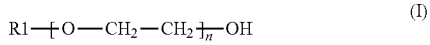

$$R1 \!\!-\!\![O\!-\!CH_2\!-\!CH_2]_{\overline{n}}\!-\!OH \quad (I)$$

where
R1 stands for an unbranched or branched, saturated or unsaturated $C_{12}$-$C_{28}$ alkyl group, preferably for a saturated, unbranched $C_{16}$ or $C_{18}$ alkyl group, and
n stands for an integer from 80 to 120, preferably for an integer from 85 to 115, more preferably for an integer from 90 to 110, and particularly preferably for an integer from 95 to 105,
and composition (B) includes the hydrocarbon(s) (b3) and the ethoxylated fatty alcohol(s) (b4) in a weight ratio (b3)/(b4) of 5:1 to 1:5, preferably of 3:1 to 1:3, more preferably of 2:1 to 1:2, and particularly preferably of 2:1 to 1:1.

The ammonia present in preparation (A) serves both as an alkalizing agent and as a swelling and penetration agent. According to the know-how of the skilled artisan, the reduction of the ammonia content has the result in general of poorer swelling of the keratin fibers and in association therewith also a poorer penetrating power of the oxidation dye precursors into the keratin fibers. For this reason, the partial replacement of ammonia by another alkalizing agent (such as alkanolamines, carbonates, or basic amino acids) is usually associated with a loss of performance of the oxidation coloring agent and is not desirable for this reason. It is preferred, therefore, if component (A) includes no alkanolamines, no carbonate salts, no hydrogen carbonate salts, and no basic amino acids.

Another preferred multi-component packaging unit (kit-of-parts) is therefore characterized in that preparation (A) is free of alkanolamines.

Alkanolamines are understood to mean aliphatic $C_1$-$C_{10}$ alkylamines, which carry one to three hydroxy groups (such as, for example, hydroxy-$C_1$-$C_{10}$-alkylamines, di(hydroxy-$C_1$-$C_5$-alkyl)amines, or tri(hydroxy-$C_1$-$C_3$-alkyl)amines). Cited as examples of alkanolamines can be particularly monoethanolamine, 2-amino-2-methylpropanol, and triethanolamine.

Understood under the definition "free of alkanolamines" in this context are preparations (A) that include less than 0.2% by weight, more preferably less than 0.1% by weight, even more preferably less than 0.05% by weight, and particularly preferably less than 0.01% by weight of alkanolamines, based on the total weight of preparation (A).

Another preferred multi-component packaging unit (kit-of-parts) is characterized in that preparation (A) is free of sodium carbonate, sodium hydrogen carbonate, potassium carbonate, potassium hydrogen carbonate, magnesium carbonate, magnesium hydrogen carbonate, ammonium carbonate, and ammonium hydrogen carbonate.

Understood under the definition "free of carbonates" in this context are preparations (A) whose total content of sodium carbonate, sodium hydrogen carbonate, potassium carbonate, potassium hydrogen carbonate, magnesium carbonate, magnesium hydrogen carbonate, ammonium carbonate, and ammonium hydrogen carbonate is below 0.2% by weight, more preferably below 0.1% by weight, even more preferably below 0.05% by weight, and particularly preferably below 0.01% by weight, based on the total weight of preparation (A).

Another preferred multi-component packaging unit (kit-of-parts) is characterized in that preparation (A) is free of the basic amino acids: arginine, lysine, ornithine, and histidine.

Understood under the definition "free of basic amino acids" in this context are preparations (A) whose total content of arginine, lysine, ornithine, and histidine is below 0.2% by weight, preferably below 0.1% by weight, more preferably below 0.05% by weight, and particularly preferably below 0.01% by weight, based on the total weight of preparation (A).

In another preferred embodiment, a multi-component packaging unit (kit-of-parts) of the invention is characterized in that
preparation (A) includes no oxidizing agent and
preparation (B) includes no other oxidizing agent apart from hydrogen peroxide.

The ready-to-use oxidative color changing agents can include furthermore additional active substances, auxiliary substances, and additives in order to improve the coloring or lightening performance and to set other desired properties of the agents.

In this case, the other facultative ingredients named below can be present in preparation (A) and/or in preparation (B) of multi-component packaging unit of the invention.

The ready-to-use coloring agents are preferably provided as a liquid preparation and another surface-active substance is therefore optionally added in addition to the agents, whereby such surface-active substances are called surfactants or emulsifiers depending on the field of application: they are preferably selected from anionic, zwitterionic, amphoteric, and nonionic surfactants and emulsifiers.

Agents suitable according to the invention are characterized in that the agent includes in addition at least one anionic surfactant. Preferred anionic surfactants are fatty acids, alkyl sulfates, alkyl ether sulfates, and ether carboxylic acids having 10 to 20 C atoms in the alkyl group and up to 16 glycol ether groups in the molecule.

Agents suitable according to the invention are characterized in that the agent includes in addition at least one zwitterionic surfactant. Preferred zwitterionic surfactants are betaines, N-alkyl-N,N-dimethylammonium glycinates, N-acylaminopropyl-N,N-dimethylammonium glycinates, and 2-alkyl-3-carboxymethyl-3-hydroxyethylimidazolines. A preferred zwitterionic surfactant is known by the INCI name Cocamidopropyl Betaine.

Agents suitable according to the invention are characterized in that the agent includes in addition at least one amphoteric surfactant. Preferred amphoteric surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids, and alkylaminoacetic acids. Especially preferred amphoteric surfactants are N-cocoalkyl aminopropionate, cocoacylaminoethyl aminopropionate, and $C_{12}$-$C_{18}$ acylsarcosine.

It has proven advantageous, furthermore, for the agents to include other non-ionogenic surface-active substances. Preferred nonionic surfactants are alkyl polyglycosides, as well as alkylene oxide adducts to fatty alcohols and fatty acids with in each case 2 to 30 mol of ethylene oxide per mole of fatty alcohol or fatty acid. Preparations with excellent properties are likewise obtained if they include fatty acid esters of ethoxylated glycerol as the nonionic surfactants.

The nonionic, zwitterionic, or amphoteric surfactants are used in proportions of 0.1 to 45% by weight, preferably 1 to 30% by weight, and very especially preferably of 1 to 15% by weight, based on the total amount of the ready-to-use agents.

The ready-to-use color changing agents can also include at least one thickener. There are no basic restrictions with regard to these thickeners. Both organic and purely inorganic thickeners may be used.

Suitable thickeners are anionic, synthetic polymers, cationic, synthetic polymers, naturally occurring thickeners, such as nonionic guar gums, scleroglucan gums or xanthan gums, gum arabic, gum ghatti, karaya gum, tragacanth gum, carrageenan gum, agar-agar, locust bean gum, pectins, alginates, starch fractions, and derivatives such as amylose, amylopectin, and dextrins, as well as cellulose derivatives such as, for example, methylcellulose, carboxyalkylcelluloses, and hydroxyalkylcelluloses, nonionic, fully synthetic polymers, such as polyvinyl alcohol or polyvinylpyrrolidinone; as well as inorganic thickeners, in particular phyllosilicates such as, for example, bentonite, in particular smectites, such as montmorillonite or hectorite.

It has proven to be advantageous, furthermore, if the coloring agents, particularly if they include in addition hydrogen peroxide, include at least one stabilizer or complexing agent. Especially preferred stabilizers are phenacetin, alkali benzoates (sodium benzoate), and salicylic acid. Furthermore, all complexing agents in the state of the art can be used. Complexing agents preferred according to the invention are nitrogen-containing polycarboxylic acids, particularly EDTA and EDDS, and phosphonates, particularly 1-hydroxyethane-1,1-diphosphonate (HEDP), and/or ethylenediamine tetramethylene phosphonate (EDTMP), and/or diethylenetriamine pentamethylene phosphonate (DTPMP), or sodium salts thereof.

Further, the agents of the invention can include other active substances, auxiliary substances, and additives, such as, for example, nonionic polymers such as, for example, vinylpyrrolidinone/vinyl acrylate copolymers, polyvinylpyrrolidinone, vinylpyrrolidinone/vinyl acetate copolymers, polyethylene glycols, and polysiloxanes; additional silicones such as volatile or nonvolatile, straight-chain, branched or cyclic, crosslinked or noncrosslinked polyalkylsiloxanes (such as dimethicones or cyclomethicones), polyarylsiloxanes, and/or polyalkylarylsiloxanes, particularly polysiloxanes with organofunctional groups, such as substituted or unsubstituted amines (amodimethicones), carboxyl, alkoxy, and/or hydroxyl groups (dimethicone copolyols), linear polysiloxanes(A)-polyoxyalkylene(B) block copolymers, grafted silicone polymers; cationic polymers such as quaternized cellulose ethers, polysiloxanes with quaternary groups, dimethyldiallylammonium chloride polymers, acrylamide-dimethyldiallylammonium chloride copolymers, dimethylaminoethylmethacrylate-vinylpyrrolidinone copolymers quaternized with diethyl sulfate, vinylpyrrolidinone-imidazolinium-methochloride copolymers, and quaternized polyvinyl alcohol; zwitterionic and amphoteric polymers; anionic polymers such as, for example, polyacrylic acids or crosslinked polyacrylic acids; structurants such as glucose, maleic acid, and lactic acid, hair-conditioning compounds such as phospholipids, for example, lecithin and kephalins; perfume oils, dimethyl isosorbide, and cyclodextrins; fiber-structure-improving active substances, particularly mono-, di-, and oligosaccharides such as, for example, glucose, galactose, fructose, fruit sugar, and lactose; dyes for coloring the agent; antidandruff agents such as piroctone olamine, zinc omadine, and climbazole; amino acids and oligopeptides; protein hydrolysates with an animal and/or vegetable base, and in the form of their fatty acid condensation products or optionally anionically or cationically modified derivatives; vegetable oils; light stabilizers and UV blockers; active substances such as panthenol, pantothenic acid, pantolactone, allantoin, pyrrolidinone carboxylic acids, and salts thereof, as well as bisabolol; polyphenols, particularly hydroxycinnamic acids, 6,7-dihydroxycoumarins, hydroxybenzoic acids, catechins, tannins, leucoanthocyanidins, anthocyanidins, flavanones, flavones, and flavonols; ceramides or pseudoceramides; vitamins, provitamins, and vitamin precursors; plant extracts; fats and waxes such as fatty alcohols, beeswax, montan wax, and paraffins; swelling and penetration agents such as glycerol, propylene glycol monoethyl ether, carbonates, hydrogen carbonates, guanidines, ureas, and primary, secondary, and tertiary phosphates; opacifiers such as latex, styrene/PVP and styrene/acrylamide copolymers; pearlescent agents such as ethylene glycol mono- and distearate and PEG-3 distearate; pigments and propellants such as propane-butane mixtures, $N_2O$, dimethyl ether, $CO_2$, and air.

The selection of these additional substances is made by the skilled artisan according to the desired properties of the agents. In regard to other facultative components and the employed amounts of said components, reference is made expressly to relevant handbooks known to the skilled artisan. The additional active and auxiliary substances are used in the agents of the invention preferably in each case in amounts of 0.0001 to 25% by weight, particularly of 0.0005 to 15% by weight, based on the total weight of the application mixture.

The ready-to-use oxidation coloring agent is prepared shortly before use by mixing (i.e., shaking, stirring, or whisking) of the two preparations (A) and (B).

If the multi-component packaging unit of the invention includes more than two components, the application mixture is prepared by mixing together of preparation (A) and (B) and all optionally still present components (e.g., by mixing of preparations (A), (B), and (C), or by mixing of preparations (A), (B), (C), and (D)). Because the mixing process (i.e., the bringing of the oxidation dye precursors into contact with the oxidizing agent) initiates the dye formation reaction, the application formulation is usually applied to the keratin fibers as far as possible immediately after the mixing process.

In a preferred embodiment, the application mixture is prepared by mixing the two preparations (A) and (B).

The two preparations (A) and (B) are typically used in the same amounts. In this case, the application mixture is obtained by mixing preparations (A) and (B) in the weight ratio of 1:1. Mixing ratios (A)/(B) of 3:1 to 3:1 are also possible, however, and according to the invention.

A further subject matter of the present invention, therefore, is a method for the oxidative coloring of keratinic fibers, comprising the following steps in the indicated sequence:
(i) mixing of two preparations (A) and (B), packaged separate from one another, of a multi-component packaging unit of the first subject matter of the invention to form a ready-to-use oxidative coloring agent,
(ii) application of the oxidative coloring agent to keratinic fibers for a time period of 1 to 60 minutes,
(I) rinsing off of the oxidative coloring agent.

Another embodiment is also a method for the oxidative coloring of keratinic fibers, comprising the following steps in the indicated sequence:
(i) mixing of two preparations (A) and (B), packaged separate from one another, of a multi-component packaging unit of the first subject matter of the invention in the mixing ratio of 3:1 to 1:3, preferably 2:1 to 1:2, and particularly preferably in the mixing ratio of 1:1,
(ii) application of the oxidative coloring agent to keratinic fibers for a time period of 1 to 60 minutes,
(I) rinsing off of the oxidative coloring agent.

An emulsion in which ammonia can be perceived only slightly in terms of odor, forms during the mixing of color preparation (A) with the oxidizing agent preparation (B). Surprisingly, a time dependence was determined hereby for the mixing process. Thus, it was found that the odor minimization is especially effective when preparation (B), which includes the long-chain fatty alcohols (b2) and hydrocarbons (b3) (and optionally the ethoxylated fatty alcohols (b4) of the formula (I)), is mixed with preparation (A) for at least 5, better at least 10, and better still at least 15 seconds.

An especially preferred embodiment, therefore, is a method for the oxidative coloring of keratinic fibers, which is characterized in that
(i) preparations (A) and (B) are mixed together for a time period of 5 to 60 seconds, preferably for a time period of 10 to 50 seconds, and particularly preferably for a time period of 15 to 40 seconds.

A still longer mixing process also has an advantageous effect on odor reduction, but for reasons of user convenience, the user will not mix preparations (A) and (B) for longer than 60 seconds.

Also if the dye formation reaction begins right after the mixing, thus it is also advantageous with respect to the odor properties of the application formulation, if the application formulation, previously prepared from (A) and (B), is allowed to stand or rest in addition for a time period of 20 seconds up to a few minutes in the closed application bottle, before the application is begun.

A time period between the end of the mixing (i) and the start of the application (ii) that is between 20 seconds and 5 minutes, preferably between 30 seconds and 4 minutes, and very especially preferably between 40 seconds and 2 minutes, has turned out to be the optimal compromise, in order both to cover the ammonia odor optimally and also not to change detrimentally the later color result.

A very especially preferred embodiment, therefore, is furthermore a method of the invention, which is characterized in that there is a time period of 20 seconds to 5 minutes, preferably a time period of 30 seconds to 4 minutes, and particularly preferably a time period of 40 seconds to 2 minutes between the mixing of preparations (A) and (B) in step (i) and the start of the application in step (ii).

The multi-component kits of the invention of the first subject matter are oxidative coloring agents, which are distinguished in that they emit only a low ammonia odor while having a very good coloring performance and excellent fastness properties. The user thus can color hair intensively and for a long time but does not perceive any strong ammonia odor during the application.

Another subject matter of the present invention for this reason is the use of a multi-component kit of the first subject matter of the invention to reduce the ammonia odor during the oxidative coloring of keratinic fibers.

The statements made about the agents of the invention apply mutatis mutandis in regard to other preferred embodiments of the method according to the invention and the use according to the invention.

EXAMPLES

1. Preparation of the Application Mixtures from (A) and (B)

The following preparation (A) was prepared:

| Preparation A, Formulation Components | (% by weight) |
|---|---|
| Lanette D [1] | 9.00 |
| Lorol $C_{12}$-$C_{18}$ techn. [2] | 3.00 |
| Texapon NSO [3] | 11.00 |
| Plantapon LGC Sorb [4] | 5.00 |

-continued

| Preparation A, Formulation Components | (% by weight) |
|---|---|
| Eumulgin B1 [5] | 0.50 |
| Ceteareth-20 [6] | 0.50 |
| Myristic acid (tetradecanoic acid) | 0.50 |
| Product W 37194 [7] | 2.00 |
| Potassium hydroxide | 1.05 |
| Sodium sulfite | 0.30 |
| Vitamin C | 0.05 |
| Hydroxyethane-1,1-diphosphonic acid (60% in water) | 0.20 |
| Ammonia (25% aqueous solution) | 5.80 |
| p-Toluylenediamine, sulfate | 1.50 |
| Resorcinol | 0.60 |
| m-Aminophenol | 0.20 |
| 3-Amino-2-methylamino-6-methoxypyridine | 0.05 |
| Water (dist.) | to 100 |

[1] $C_{16}$-$C_{18}$ fatty alcohol (INCI name: Cetearyl alcohol) (Cognis)
[2] $C_{12}$-$C_{18}$ fatty alcohol (INCI name: Coconut alcohol) (Cognis)
[3] Sodium lauryl ether sulfate, ethoxylated with 2 EO (aqueous solution, active substance content 27% by weight)
[4] Lauryl glucoside (10-20% by weight), sodium lauryl glucose carboxylate (15-25% by weight), water (62-67% by weight)
[5] $C_{16}$-$C_{18}$ fatty alcohol, ethoxylated (12 EO) (INCI name: Ceteareth-12) (BASF)
[6] $C_{16}$-$C_{18}$ fatty alcohol, ethoxylated (20 EO)
[7] N,N,N-Trimethyloxo-3-[(1-oxo-2-propenyl)amino]-1-propanaminium chloride, polymer with sodium 2-propenoate (INCI: Acrylamidopropyltrimonium chloride/Acrylate Copolymer), 20% by weight aqueous solution The following preparations B were prepared:

| Preparation B, Formulation Components | V (% by weight) | E (% by weight) |
|---|---|---|
| Cetearyl alcohol | 1.80 | 3.70 |
| Behenyl alcohol | — | 1.30 |
| PEG-40 Castor Oil | 0.40 | — |
| Liquid paraffin | — | 0.65 |
| Sodium cetearyl sulfate | 0.,20 | — |
| Steareth-100 | — | 0.60 |
| Ceteareth-30 ($C_{16}$-$C_{18}$ fatty alcohol, ethoxylated (30 EO)) | — | 0.50 |
| Glyceryl monostearate | — | 0.50 |
| Hydroxyethane-1,1-diphosphonic acid (60% in water) | 0.25 | 0.25 |
| Cocoamidopropylbetaine (32% solution in water) | 0.40 | 0.40 |
| Disodium pyrophosphate | 0.20 | 0.20 |
| Hydrogen peroxide (50% solution in water) | 12.0 | 12.0 |
| Water (dist.) | to 100 | to 100 |

Preparation (A) and preparation (B) were shaken together in the weight ratio of 1:1 for 30 seconds in a closed application bottle. The preparation prepared from preparations (A) and the comparison formulation (B) was applied directly to hair. The application mixture prepared from preparation (A) and preparation (B) of the invention was first allowed to stand for 2 minutes in the closed application bottle and then applied to hair.

2. Determination of the Ammonia Odor

In each case 10 minutes after the start of the application of the particular application mixtures to hair, the ammonia odor was evaluated by 5 trained persons. The evaluation occurred under blind conditions, which means that the persons performing the evaluation did not know which formulation they were evaluating. The average was determined from the individual evaluations.

The ammonia odor was rated on a scale of 0 (virtually no odor perceptible) to 10 (very strong ammonia odor).

TABLE 4

| Ammonia odor during the application | | |
|---|---|---|
| | A + B (comparison) | A + B (according to the invention) |
| Covering up of ammonia | 5 | 3 |

It is clear that the ammonia odor during application of the application formulation of the invention was perceived as considerably reduced.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A multi-component packaging unit that is a kit-of-parts for the oxidative coloring of keratinic fibers, wherein the multi-component packaging unit comprises:
   a preparation (A) and a preparation (B), wherein preparations (A) and (B) are packaged separate from one another, and wherein;
   (a) preparation (A) comprises:
      a cosmetic carrier
      (a1) at least one oxidation dye precursor and
      (a2) ammonia,
   and
   (b) preparation (B) comprises:
      a cosmetic carrier
      (b1) hydrogen peroxide,
      (b2) at least one fatty alcohol from the group comprising arachidyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), heneicosyl alcohol (heneicosan-1-ol), behenyl alcohol (docosan-1-ol), erucyl alcohol ((13Z)-docos-13-en-1-ol), and/or brassidyl alcohol ((13E)-docosen-1-ol), and
      (b3) one or more of paraffin oil(s) and paraffin wax(es) having 8 to 80 C atoms in a total amount of 0.1 to 4.5% by weight based on the total weight of preparation (B); and
      (b4) at least one ethoxylated fatty alcohol of the formula (I),

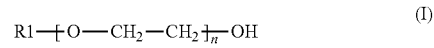

$$R1 \!-\!\!\left[\!O\!-\!CH_2\!-\!CH_2\!\right]_n\!\!-\!OH \quad (I)$$

wherein
R1 is an unbranched or branched, saturated or unsaturated $C_{12}$-$C_{28}$ alkyl group, and
n is an integer from 80 to 120; and
wherein a weight ratio of (b2) to (b4) is from 5:1 to 1:1.

2. The multi-component packaging unit according to claim 1, wherein:
the at least one fatty alcohol (b2) comprises arachidyl alcohol (eicosan-1-ol) in a total amount of 0.2 to 6.4% by weight based on the total weight of preparation (B).

3. The multi-component packaging unit according to claim 1, wherein preparation (B) includes as (b3) the one or more of paraffin oil(s) and paraffin wax(es) in a total amount of 0.4 to 4.5% by weight based on the total weight of preparation (B).

4. The multi-component packaging unit according to claim 1, wherein preparation (B) includes the at least one fatty alcohol (b2) and the one or more of paraffin oil(s) and paraffin wax(es) (b3) in a weight ratio (b2)/(b3) of from 3:1 to 2:1.

5. The multi-component packaging unit according to claim 1, wherein:
a weight ratio of (b3) to (b4) is from 2:1 to 1:1; and
the weight ratio of (b2) to (b4) is from 3:1 to 2:1.

6. The multi-component packaging unit according to claim 1, wherein preparation (B) includes the at least one ethoxylated fatty alcohol (b4) of the formula (I) in a total amount of 0.1 to 5.5% by weight based on the total weight of preparation (B).

7. The multi-component packaging unit according to claim 1, wherein preparation (A) is free of ethoxylated fatty alcohols of the formula (I).

8. The multi-component packaging unit according to claim 1, wherein composition (B) includes the at least one fatty alcohol (b2) and the at least one ethoxylated fatty alcohol (b4) of the formula (I) in the weight ratio (b2)/(b4) of from 3:1 to 2:1, a weight ratio of (b3) to (b4) is from 2:1 to 1:1, and a weight ratio of (b2) to (b3) is from 3:1 to 2:1.

9. The multi-component packaging unit according to claim 1, wherein composition (B) includes the one or more of paraffin oil(s) and paraffin wax(es) (b3) and the at least one ethoxylated fatty alcohol (b4) in a weight ratio (b3)/(b4) of 5:1 to 1:5.

10. The multi-component packaging unit according to claim 1, wherein preparation (A) is free of alkanolamines.

11. The multi-component packaging unit according to claim 1, wherein
preparation (A) includes no oxidizing agent and
preparation (B) includes no other oxidizing agent apart from hydrogen peroxide.

12. A method for the oxidative coloring of keratinic fibers, comprising, in the indicated sequence:

(i) mixing two preparations (A) and (B), packaged separate from one another, of a multi-component packaging unit to form a ready-to-use oxidative coloring agent, wherein;
preparation (A) comprises:
a cosmetic carrier;
(a1) at least one oxidation dye precursor; and
(a2) ammonia (a2);
and
preparation (B) comprises;
a cosmetic carrier;
(b1) hydrogen peroxide;
(b2) at least one fatty alcohol from the group comprising arachidyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), heneicosyl alcohol (heneicosan-1-ol), behenyl alcohol (docosan-1-ol), erucyl alcohol ((13Z)-docos-13-en-1-ol), and/or brassidyl alcohol ((13E)-docosen-1-ol);
(b3) one or more of paraffin oil(s) and paraffin wax(es) having 8 to 80 C atoms in a total amount of 0.1 to 4.5% by weight based on the total weight of preparation (B); and
(b4) at least one ethoxylated fatty alcohol of the formula (I),

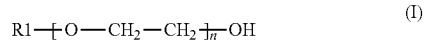

wherein
R1 is an unbranched or branched, saturated or unsaturated $C_{12}$-$C_{28}$ alkyl group, and
n is an integer from 80 to 120; and
wherein a weight ratio of (b2) to (b4) is from 5:1 to 1:1;
(ii) applying the oxidative coloring agent to keratinic fibers for a time period of 1 to 60 minutes, and
(iii) rinsing off of the oxidative coloring agent.

13. The method according to claim 12, wherein preparations (A) and (B) are mixed together in step (i) for a time period of 5 to 60 seconds.

14. The method according to claim 12, wherein there is a time period of 20 seconds to 5 minutes between the mixing of preparations (A) and (B) in step (i) and the start of the application in step (ii).

* * * * *